(12) United States Patent
Van Der Westhuizen et al.

(10) Patent No.: US 6,288,291 B1
(45) Date of Patent: Sep. 11, 2001

(54) FLUORINATION

(75) Inventors: Driekus Van Der Westhuizen, Pretoria (ZA); Petrus Johannes Venter, Calgary (CA)

(73) Assignee: South Africa Nuclear Energy (ZA)

( * ) Notice: Subject to any disclaimer, the term of this patent is extended or adjusted under 35 U.S.C. 154(b) by 0 days.

(21) Appl. No.: 09/573,863

(22) Filed: May 18, 2000

(30) Foreign Application Priority Data

May 20, 1999 (ZA) ........................................ 99/3445

(51) Int. Cl.$^7$ ........................................ C07C 19/08
(52) U.S. Cl. ........................ 570/134; 560/187; 562/602
(58) Field of Search ........................ 570/134; 560/187; 562/602

(56) References Cited

U.S. PATENT DOCUMENTS 5,578,278 * 11/1996 Fall et al. .
5,674,949 10/1997 Bierschenk ........................ 525/331.6

FOREIGN PATENT DOCUMENTS 0396168 11/1990 (EP) .
0646557 4/1995 (EP) .

\* cited by examiner

*Primary Examiner*—Gary Geist
*Assistant Examiner*—Hector M Reyes
(74) *Attorney, Agent, or Firm*—Ladas & Parry

(57) ABSTRACT

A process for fluorinating a hydrocarbon substrate by mixing it with an inert diluent and mixing the diluted substrate with a gaseous fluorinating reagent to form a foam reaction mixture. The fluorinating reagent reacts with the substrate in the form to foam product. The foam is separated into a liquid component which contains product and a gas component. Product is withdrawn from the liquid component which is then returned to the diluting step. Fluorinating reagent is fed into the gas component which is then recirculated to the mixing step.

16 Claims, 1 Drawing Sheet

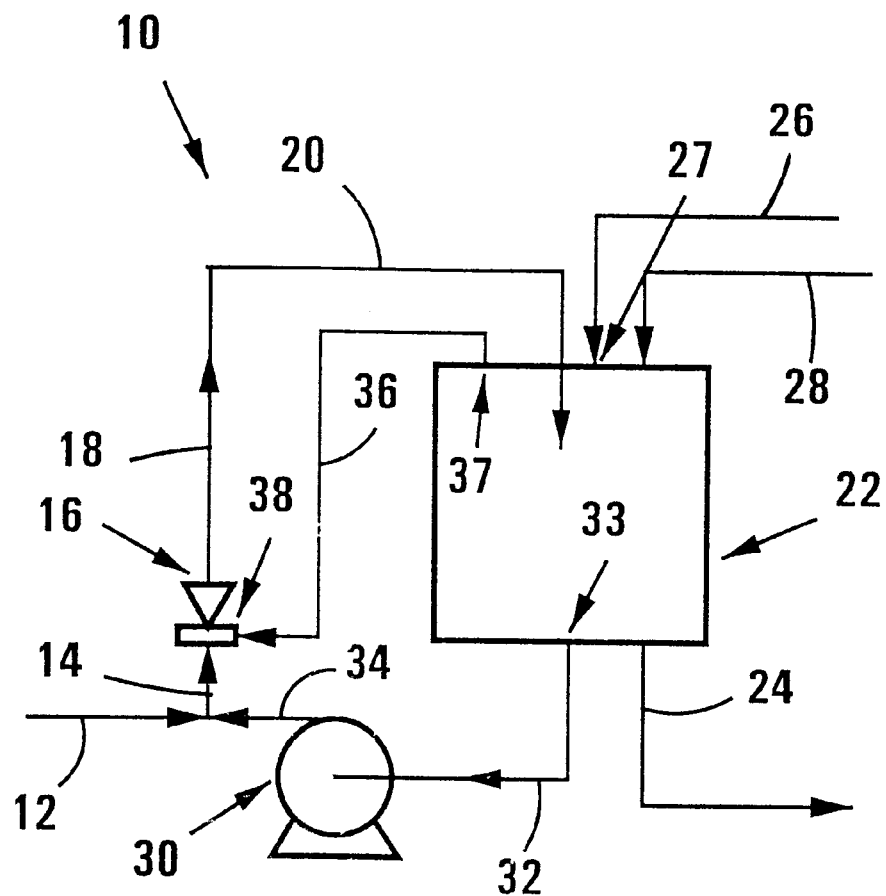

FLUORINATION

This invention relates to the fluorination of a hydrocarbon substrate. More particularly, it relates to a process and installation suitable for the perfluorination of an optionally substituted hydrocarbon substrate.

According to one aspect of the invention there is provided a process for the fluorination of an optionally substituted hydrocarbon substrate, the process including the steps of:
diluting a hydrocarbon substrate feed with an inert diluent liquid to form a diluted substrate;
mixing the diluted substrate with a gaseous fluorinating reagent to form a reaction mixture which is a foam;
allowing the fluorinating reagent to react in the foam with the substrate, to fluorinate the substrate to obtain fluorinated product material;
separating the foam containing the fluorinated product material into a gas component and a liquid component, the liquid component containing the fluorinated product material;
withdrawing the fluorinated product material from the liquid component and returning the liquid component from which the fluorinated product material has been withdrawn to the diluting step where it acts as the diluent liquid;
feeding a feed of the fluorinating reagent into the gas component; and
recirculating the gas component containing the fluorinating reagent feed to the mixing step where it provides the fluorinating reagent in the reaction mixture.

Diluting the substrate feed with the diluent liquid may be such as to form a solution, emulsion or suspension of the substrate in the diluent liquid, which diluent liquid forms a continuous phase and acts as a carrier for the substrate. By inert in the context of the diluent liquid of the present invention is meant that the diluent liquid undergoes no unacceptable chemical reactions and preferably undergoes no chemical reactions whatsoever, during the operation of the process. Preferably the substrate feed is fed into a stream of the diluent liquid which is undergoing turbulent flow, upstream of the mixing step and no further from the mixing step than is necessary to provide a sufficiently homogenous liquid feed into the mixing step. In particular, the feeding of the hydrocarbon substrate may be into a stream of the liquid component which is undergoing turbulent flow, the feeding of the hydrocarbon substrate being at a position between the separating step and the mixing step.

Conveniently returning of the liquid component to the diluting step is by pumping the liquid component, from the separating step to the diluting step, at a rate sufficient to cause turbulent flow in the pumped liquid component, the hydrocarbon substrate feed being fed into the turbulent flow of the pumped liquid component with the hydrocarbon substrate feed in liquid form, although, in principle, the substrate may be in gaseous or finely divided solid form, provided that it is sufficiently dissolved or otherwise dispersed in the diluent liquid by the time the mixing step takes place.

The mixing is preferably flash mixing, conveniently by passing the diluted substrate and the fluorinating reagent together through an in-line continuous mixer such as a static mixing device, which is conveniently in the form of a jet pump of the ejector, eductor or extractor type and may include a venturi. By flash mixing is meant that the mixing should be by a mixing step which progresses substantially to completion in at most 1 second.

Any suitable gaseous fluorinating reagent may be used, such as oxidizing fluorine-containing chemicals. The gaseous fluorinating agent may thus be selected from the group of fluorinating gases selected from $F_2$, $UF_6$, $XeF_2$, $ClF_3$ and $BrF_3$, molecular fluorine as $F_2$ typically being preferred, for reasons of yield, cost and availability. To facilitate control over the reaction step, which is exothermic, the fluorinating gas may be diluted by means of an inert diluent gas, which may be a noble inert gas such as argon, but which, again for reasons of cost and availability, is preferably nitrogen. In other words, the gaseous fluorinating reagent, when it is mixed with the diluted substrate may also be in dilute form, the gaseous fluorinating reagent being diluted with an inert diluent gas. The gas component which is recirculated is thus usually an $F_2/N_2$ mixture in which the $F_2$ forms 10–80% by volume, preferably 30–60% by volume, eg 50%, a suitable or optimum value being determined by routing experimentation. The ratio of gas:liquid mixed together in the mixing step may be 2:1–1:50 by volume, preferably 1:2–1:10, eg 1:4, the consistency of the foam being determined thereby. In a particular embodiment of the invention, the gaseous fluorinating reagent may be $F_2$, being in the form of part of an essentially $F_2/N_2$ gas mixture in which $N_2$ is an inert diluent gas, when the gaseous fluorinating reagent is mixed with the diluted substrate, the gas mixture including 10–80% by volume $F_2$ and 20–90% by volume $N_2$, the volume ratio in the mixing step of the gas mixture:diluted substrate being 2:1–1:50 by volume.

Allowing the fluorinating reagent to react in the foam with the substrate preferably includes keeping the reaction mixture in the form of a foam, without unacceptable separation thereof into liquid and gaseous components, until the reaction has proceeded to an acceptable degree of completion. The Applicant has found that discharging the reaction mixture from the mixing step into a downwardly, or preferably upwardly extending, but no horizontal, flow path, such as a conduit in the form of a pipe, promotes retention of a foam which is resistant to separation into liquid and gaseous components. Thus, allowing the fluorinating reagent to react in the foam with the substrate may include causing the reaction mixture to pass, in the form of a foam, along a flow path leading from the mixing step to the separating step, the flow path being inclined at an angle to the horizontal and the fluorinating agent reacting in the foam with the substrate as the foam moves along the flow path. When the foam is discharged vertically upwardly from the mixing step along a conduit of circular cross-section, a diameter:length ratio in the vertical conduit be of 1:15–1:40 is typically adequate. Routine experimentation can be used to establish optimum or acceptable values for conduits of different cross-sectional outlines or at different inclinations to the horizontal. In a particular embodiment and for conduits of any cross-sectional outline, the flow path may be inclined by an angle of at least 45°, preferably at least 80°, to the horizontal, the numerical ratio of the cross-sectional flow area in $mm^2$ of the flow path to its length in mm being in the range $\pi/4:15–\pi/4:40$.

The separating step may be a settling step in which the foam separates and settles in to a liquid layer below a gaseous header space or freeboard. Fluorinate product material and returned liquid component may be withdrawn from this liquid layer, while recirculated gaseous component can be withdrawn from the header space or freeboard, into which freeboard the gaseous fluorinating reagent feed may be fed. In particular, thus, the separation step may be a settling step in which the foam is allowed to settle into a layer of liquid component below a header space containing the gas component, fluorinated product material and returned liquid component being withdrawn from the liquid layer, recirculated gas component being withdrawn from the header space, and a feed of the gaseous fluorinating reagent being fed into the header space. Fluorinated product material will be withdrawn as part of a mixture of diluent liquid, fluorinated product material and partially reacted substrate in the form of intermediates. Fluorinated product material can be separated from this mixture, the residue formed from diluent liquid and partially reacted substrate/intermediates being reintroduced into the liquid component. Thus, in other words, the fluorinated product material and returned liquid component may be withdrawn as a mixture from the liquid layer, the process including separating the fluorinated product material form the liquid component after withdrawal thereof from the liquid layer and before the liquid component enters the diluting step in which it dilutes the substrate feed.

In the liquid component there is a possibility that molecules of substrate, or of partially reacted substrate, can react together and polymerise or oligomerize, which is undesirable. This polymerization or oligomerization is suppressed by use of the diluent liquid to separate molecules of the substrate and molecules of partially reacted substrate from one another and by intimate mixing of the liquid component with the gas component, preferably such as to form a foam. Thus, the liquid component should remain separated from the gaseous component of the foam for as short a time as possible, the residence time of the liquid component in the separating step being kept as short as possible, as should be the time taken for the liquid component to be fed from the separating step to the mixing step, and also from the reaction step in the foam to the separating step, as separating can take place prior to the separating step. In particular, the residence time of the liquid component in the separating step and the residence time of the liquid component in the liquid component returning step, after the liquid component leaves the separating step and until it enters the mixing step, may typically amount in total to at most 10 seconds. In general, however, the upper limit of said total residence time will be determined by the nature of the substrate and of the dilent liquid employed. An appropriate residence time should thus be determined, for each fluorinated product material to be made, by routine experimentation, taking commercial and practical considerations into account, in particular the need to avoid or limit the irreversible formation of undersirable by-products.

As far as process parameters are concerned, the reaction step may be carried out under an elevated pressure in a range extending from the vapour pressure of the diluent liquid at the reaction temperature up to 28 MPa, preferably 200–700 kPa, eg 400 kPa. The reaction temperature in turn may be −40° C. to 80° C., conveniently −30° C. to 50° C., eg 20° C. Typically, allowing the fluorinating reagent to react in the foam with the hydrocarbon substrate may be at a reaction pressure of 200–700 kPa and at a reaction temperature of between −10° C. and 50° C. A suitable inert diluent liquid has been found to be hydrofluoric acid (HF) and the substrate may be added to the recirculated liquid component at a rate such that a dilution of substrate in diluent liquid of 1:20 000–1:300 000 or higher is obtained, conveniently 1:50 000–1:300 000, eg 1:160 000. In other words, the feeding of the hydrocarbon substrate feed into the inert diluent liquid may be in a proportion such that a dilution of the substrate by the diluent liquid is obtained whereby the volume ratio of substrate:diluent liquid in the diluted substrate is in the range 1:50 000–1:300 000.

As indicated above, the hydrocarbon substrate is optionally substituted. Suitable substrates which can be fluorinated or perfluorinated (ie fully fluorinated) in accordance with the process of the present invention thus include unsubstituted saturated and unsaturated hydrocarbons such as aromatic hydrocarbons, containing alkyl and/or aryl groups, or they may be substituted hydrocarbons, examples being halogenated hydrocarbons, carboxylic acid halides, sulphonic acid halides, ethers, esters, etc. Typically any unsaturated bonds in the substrate will be converted to saturated bonds by the fluorination. In short, the substrate may be selected from the group of unsubstituted hydrocarbons consisting of alkyl compounds and aryl compounds, and from the group of substituted hydrocarbons consisting of halogenated hydrocarbons, carboxylic acid halides, sulphonic acid halides, ethers and esters. As indicated above, the preferred inert diluent liquid is hydrogen fluoride (HF), as it is usually sufficiently inert for this purpose and is compatible with the process and with materials used in the installation described below.

According to another aspect of the invention there is provided an installation for the fluorination of an optionally substituted hydrocarbon substrate, for example by means of the process described above, the installation being a liquid flow circuit including:

a dilution stage for separately receiving a hydrocarbon substrate feed and a diluent liquid, for diluting the substrate with the diluent liquid;

a mixing stage in fluid flow communication with the dilution stage for separately receiving diluted hydrocarbon substrate feed from the dilution stage and for receiving a gaseous fluorinating reagent, for mixing the diluted hydrocarbon substrate feed with the gaseous fluorinating reagent to form a reaction mixture which is a foam;

a reaction stage in fluid flow communication with the mixing stage for receiving foam for the mixing stage and for allowing the fluorinating reagent to react with the substrate in the reaction mixture, to fluorinate the substrate and form fluorinated product material; and a separation stage in fluid flow communication with the reaction stage, and having a liquid flow connection to the dilution stage and gas flow connection to the mixing stage, for receiving foam containing fluorinated product material from the reaction stage, for separating the foam into a gas component and a liquid component, for feeding separated liquid component as diluent to the dilution stage (to provide the fluorinating reagent), and for feeding separated gas component containing the gaseous fluorinating reagent to the mixing stage, the installation including liquid returning means for returning separated liquid component from the separation stage to the dilution stage to cause it to flow around the liquid flow circuit including the dilution stage, the mixing stage, the reaction stage and the separation stage, and the installation including as recirculation means for recirculating separated gas component from the separation stage to the mixing stage, the installation also including a substrate liquid feed line into the circuit and a fluorinating reagent fluid gas feed line for feeding fluorinating reagent into the gas flow connection between the reaction stage and the mixing stage.

The substrate liquid feed line may feed into the dilution stage, the fluorinating reagent gas feed line feeding into the separation stage.

More particularly, the mixing stage may be provided by a static mixing device such as a jet pump comprising a venturi, flow of diluted substrate in use through the venturi acting to withdraw and recirculate gaseous component from the separating stage to the venturi, so that the jet pump acts as the gas recirculating means for recirculating the gaseous component. It follows that the mixing stage may include an in-line continuous mixer, such as a static mixer, having no moving parts; and, in particular, the continuous mixer may be in the form of a jet pump connected in-line in the circuit between the dilution stage and the reaction stage to employ diluted substrate flowing from the dilution stage to the reaction stage as its pumping liquid, the jet pump having a gas suction inlet in communication with the separation stage and with the fluorinating reagent gas feed line, and the jet pump acting as the gas recirculation means. The connection of the suction chamber inlet to the fluorinating reagent gas feed line may be direct, or indirect via the separation stage. The liquid returning means for returning the liquid component may be a pump arranged to pump returned liquid component at a turbulent flow rate through the dilution stage and to the mixing stage along a conduit which receives the substrate feed and which conduit, between the substrate feed and the mixing stage, acts as the dilution stage.

The reaction stage may also be a conduit, such as a pipe of circular cross-section, extending upwardly, preferably vertically, from the venturi, the pipe having a diameter: length ratio of preferably 1:15–1:40, more preferably 1:20–1:35, eg 1:28. In general, the reaction stage may be a conduit included by an angle of at least 45°, preferably at least 80°, to the horizontal, the conduit having, for any cross-sectional outline thereof, a cross-sectional flow area and a length such that the numerical ratio of the cross-sectional flow area in $mm^2$ to the length of the conduit in mm, is in the range $\pi/4{:}15$–$\pi 4{:}40$, in particular being a substantially vertical (ie inclined at more than 80° to the horizontal) pipe of circular cross-section having a diameter: length ratio of 1:20–1:35.

The separation stage may be a settling tank, which may be arranged alongside the venturi and the pipe which forms the reaction stage, preferably arranged so that the flow line along which the pump pumps the liquid component from the settling tank to the venturi is as short as practicable, bearing in mind that the substrate feed should be far enough from the venturi to allow substrate to be adequately homogeneously diluted or dispersed by the liquid component before entering the venturi, but close enough to the venturi to resist and preferably to prevent undesirable side reactions such as polymerization or oligomerization, and the flow path from the top of the reaction stage pipe to the separation stage should also be as short as practicable. This is to keep the time that the liquid component is not foamed with the gaseous component as short as possible to resist undesirable polymerization or oligomerization of substrate molecules which are not yet perfluorinated. It follows that the separation stage may be a settling stage having a low level liquid outlet to the dilution stage, a high level gas outlet to the mixing stage and a high level fluorinating reagent gas feed inlet; and the part of the circuit between the separation stage and the dilution stage may be as short as practicable, the dilution stage in turn being arranged to feed diluted substrate into the mixing stage as soon as practicable after dilution is complete, so that the time spent by diluted substrate in the circuit, other than as a constituent of the foam, is preferably at most 30 seconds. The fluorinating as feed may be into the header space or freeboard of the settling tank, as may be an inert gas feed, for feeding an inert diluent gas such as nitrogen to the gaseous component. When the liquid component is slow to settle, the separation stage may include a dynamic separation device such as a cyclone (hydrocyclone), to accelerate the separation step. As indicated above with regard to the process of the present invention, this upper time limit will be determined by routine experimentation, bearing in mind the nature of the substrate and of the diluent liquid used, together with practical and economic considerations and the need to avoid undesirable by-products. Although in the majority of cases short times are desired, it is contemplated that, when the substrate and diluent liquid are such that a more or less indefinitely long setting time can be employed, long residence times can be acceptable, which demonstrates the flexibility of the process of the invention.

In this regard it is contemplated that, while the process of the present invention will be operated on a nominally continuous basis, it can be regarded as a quasi-batch type process because of impurities which may be present in any fluorinating gas feed such as a molecular fluorine ($F_2$) feed, as well as volatile breakdown products that may form during the fluorination step. Build-up of such impurities will thus necessitate a periodic blow-down of the circuit formed by the installation, followed by a new start-up of the process. Naturally, if the fluorinating gas purity is sufficiently high and acceptably low quantities of volatile breakdown products are formed, no periodic blow-down may be required, or such blow-downs may be exceptional and occasional, being separated by long time intervals. Nitrogen will typically be fed to the gas component in the settling tank at start-up to dilute the fluorine, after which it is expected that no further nitrogen will be fed until the next start-up or after the succeeding blow-down, if required, although, naturally, substrate and fluorine will be continuously fed to the process, as they are consumed, while the process is in operation. Nitrogen consumption is expected to be acceptably low and no replenishment is expected during operation, before blow-down. If required, it can take place after a blow-down or at the next start-up.

The general configuration of the installation of the present invention affords flexibility with regard to reaction conditions, which permits optimization for a variety of products, and promotes ease of process control and a desirable degree of safety.

The invention will now be described, by way of non-limiting example, with reference to the accompanying schematic drawing in which the single FIGURE shows a schematic flow diagram of an installation according to the present invention, for carrying out a process according to the invention, and the invention will also be described with reference to the following worked Example.

In the drawing, reference numeral 10 generally designates an installation according to the invention for carrying out a process according to the invention. In the installation 10 a substrate feed flow line is a conduit of circular outline designated 12 is shown feeding into the upstream end of a dilution stage in the form of a flow line in the form of a conduit of circular outline designated 14.

The flow line 14 feeds into a mixing stage in the form of a jet pump 16 including a venturi which in turn feeds into a reaction stage in the form of a flow line 18 provided by a vertically upwardly extending pipe of circular cross-section and having a diameter:length ratio of 1:28. The upper end of the pipe 18 feeds into a horizontally extending flow line 20, whose downstream end feeds downwardly into a separation stage in the form of a settling tank 22.

A fluorinated product material take-off flow line 24 leads from the bottom of the tank 22, and a fluorine gas feed line 26 and a nitrogen gas feed line 28 feed respectively into the top of the tank 22, the fluorine feed line feeding at a high level inlet 27 into the tank 22. A pump 30 is provided, having an inlet fed by a flow line 32 from a low level outlet 33 from the bottom of the tank 22, the pump 30 having an outlet feeding into a low line 34 which in turn feeds into the upstream end of the flow line 14. Although not explicitly shown in the drawing the various parts of the installation 10 are arranged so that flow lines 14, 20, 32 and 34 are as short as practicable, flow line 14 in particular being no longer than is required for adequate mixing and dilution of substrate feed from flow line 12, with liquid flow from flow line 34, before the diluted flow enters the jet pump 16. A gas flow line 36 extends from a high level outlet 37 at the top of the tank 22 to a gas inlet 38 of the jet pump 16.

In use, at start up, the tank 22 is charged with a suitable volume of diluent liquid, such as the hydrogen fluoride mentioned hereunder, and the header space or freeboard in the tank above the diluent liquid is charged with a suitable fluorine/nitrogen gas mixture, such as a 50:50 by volume mixture, with fluorine from flow line 26 and nitrogen from flow line 28.

The process of the present invention is set in operation by using the pump 30 to pump liquid from the tank 22 along flow lines 32, 34 and 14 to the jet pump 16, while substrate is fed from an external supply along flow line 12 into flow line 14, fluorine is fed from an external supply along flow line 26 to the tank 22, and liquid is withdrawn from tank 22 along line 24. During operation no nitrogen is fed along flow line 28, but the jet pump 16 acts to withdraw gas from the freeboard of the tank 22 via flow line 36 and recirculate it into the gas inlet 28 of the pump 16 and thence into the flow line/reaction stage 18.

Diluent liquid and substrate feed mix rapidly in flow line 14, whose contents are kept turbulent by the pump 12 which is operated at an output rate sufficient to cause turbulent flow in the line 14. Mixed substrate and diluent liquid are in turn mixed vigorously in the jet pump 16 with gas from flow line 36 to form a continuous foam, which foam fully occupies and fills flow line 18, up which it rises. This foam passes from flow line 18 along flow line 20 to tank 22, where gas-liquid separation is allowed to take place.

Fluorination of the substrate takes place in the flow line 18, and is taken as close as practicable to completion in flow line 20 and tank 22. A liquid layer (not shown) forms in the bottom of the tank 22, containing diluent liquid, partially reacted substrate (partially fluorinated product material) and fully fluorinate product material, ie perfluorinated product material, and dissolved (to saturation) reaction gas ($F_2$ and $N_2$).

Substrate is fed along line 12 and fluorine is fed along line 28, at rates which correspond to the rate of fluorination of the substrate in flow lines 18 and 20 and in tank 22, while fluorinated product material is withdrawn from tank 22 along line 24 at the rate at which fluorinated product, eg perfluorinated product, is formed by the fluorination. Fluorinated product material take-off is passed to a separate state (not shown) such as a distillation column, where fluorinated product material is separated from diluent liquid and partially fluorinated product material, which diluent liquid and partially fluorinated product material are reintroduced into the tank 22. Liquid is returned from the tank 22 by the pump 30 via lines 30 and 34 to the diluting step in the line 14.

It has been found that regulation of the fluorinating gas feed rate is conveniently by means of a pressure regulating valve (not shown) at the inlet 27 to the tank 22 from the line 26, to obtain a constant desired pressure in the tank 22. This is because may drop in pressure in the installation, which forms a closed circuit, arises from a drop in the partial pressure of the fluorine gas as a consequence of the fluoridation of the substrate. The fluorine gas feed rate thus depends directly on the substrate feed rate, and is self-regulating, provided that the pressure in the circuit is kept constant. The feed rate of the substrate in turn is regulated so that, bearing in mind heat generation caused by the fluoridation of the substrate in the installation, the temperature in the installation remains within a acceptable range.

The installation and process can be operated in accordance with the following Examples.

EXAMPLE 1

Perfluorination of n-Hexane

In an installation according to the drawing, with a total volume excluding flow lines 12, 26, 28 and 24 of 8 liters, 6 kg of anhydrous hydrofluoric acid (hydrogen fluoride or HF) was loaded into the tank 22. The pump 30 was then used to pump this liquid around the circuit constituted by the tank 30, venturi pump 16 and flow lines 14, 18, 20, 32 and 34, at a rate of 60 kg/minute, so that the hydrofluoric acid circulated around the circuit 10 times/minute, thus having a residence time in the circuit as a whole, and in the separating step, in the recycling step and in the dilution step taken together of at most 6 seconds.

The tank 22 was charged with nitrogen to a pressure of 200 kPa, and the fluorine was then slowly charged into the tank 22 until a pressure of 400 kPa was reached, to obtain a gas mixture in the tank having an $F_2:N_2$ ratio of 50:50 by volume. The tank 22 was set at a temperature controlled at 20° C.

Dried n-hexane was pumped by means of a piston pump (no shown) via line 12 into the circuit at a rate of 500 µl/minute, while fluorine was fed to tank 22 at a rate sufficient to maintain the 400 kPa pressure therein. A slight rise in the temperature in the tank 22 was then noted, together with a surge in fluorine feed along line 26. Liquid was withdrawn along line 24 from tank 22 at a rate sufficient to maintain a constant low liquid level in the tank 22, and such that no foam was withdrawn.

Liquid withdrawn from the tank along line 24 was allowed to settle and separated into two layers, the bottom layer of which was perfluorated hexane. This was purified by distillation, partially fluorinated product material being returned to the tank 22 while heavier oligomeric waste products were discarded. The upper layer which settled out was distilled to obtain purified hydrofluoric acid, suitable for returning to the pipe 14 or for use elsewhere, while other distillation fractions from the distillation of the upper layer, containing partially fluorinated substrate, were also returned to the tank 22.

A perfluorinated hexane yield of 85% of theoretical, with a fluorine loss of less than 2%, was obtained.

EXAMPLE 2

Perfluorination of Octanoyl Fluoride

Example 1 was repeated, except that octanoyl fluoride was fed, via line 12, at 300 µl/minute as the substrate into HF as the diluent liquid. Again a 50:50 ratio of $F_2:N_2$ was used with a total reaction pressure of 400 kPa. The reaction temperature was controlled to be between 31 10° C. and −5° C. Liquid was withdrawn continuously from line 24 to keep the level in the settling tank 22 constant. The product mixture was distilled to separate the HF from organic components thereof. The perfluorinated product so obtained was further purified by removal of by-products therefrom by means of another distillation. Under non-optimised conditions a yield of 62% perfluorooctanoyl fluoride product material was obtained.

EXAMPLE 3

Perfluorination of 3-Methoxy-Tetrafluoropropanoic Acid Methyl Ester

Example 1 was repeated to perfluorinate 3-methoxy-tetrafluoropropanoic acid methyl ester as substrate, the substrate being fed via line 12 at 900 µl/minute into HF as the diluent liquid. A 40:60 ratio of $F_2:N_2$ was used with a total reation pressure of 350 kPa. The reaction temperature was controlled to be between 4° C. and 10° C. Liquid was withdrawn continuously from line 24 to keep the level in the settling tank 22 constant. The intended product was found to be very unstable in an undiluted form. In the presence of an appropriate nucleophile de-esterification was found to take place to yield the acid fluoride and carboxyl difluoride. To analyse the product, a methoxy ester was formed. This was done by first separating the organic products from the HF. Thus, a sample of the product mixture was added to methanol and was allowed to react therewith. The mixture so obtained was drained into ice and allowed to separate into layers. The bottom organic layer was isolated and remixed with additional methanol and potassium fluoride. This mixture was then stirred for 6 hours. After a further wash and subsequent drying with sodium sulphate followed by filtration, the methoxy ester was analysed. Under non-optimized conditions a yield of 47% 3-trifluoromethoxy-tetrafluoropropanoic acid methyl ester was obtained.

EXAMPLE 4

Perfluorination of 2- Methoxy-Tetrafluoropropanoic Acid Methyl Ester

Example 1 was repeated to perfluorinate 2-methoxy-tetrafluoropropanoic acid methyl ester substrate. This substrate was fed, via line 12 at 900 µl/minute into HF as the diluent liquid. A 40:60 ratio of $F_2:N_2$ was used with a total reaction pressure of 350 kPa. The reaction temperature was controlled to be between 4° C. and 10° C. Liquid was withdrawn continuously from line 24 to keep the level in the settling tank 22 constant. A sample of the product mixture was added to methanol and allowed to react therewith. The mixture so obtained was drained into ice and allowed to separate into layers. The bottom organic layer was isolated and dried over sodium sulphate followed by filtration. This filtered material was distilled at a temperature between 32° C. and 34° C. to obtain a product material fraction. Under non-optimized conditions a yield of 35% perfluoro-(2-methoxy-propanoic acid methyl ester) was obtained.

It is an advantage of the present invention, particularly as described with reference to the accompanying drawing and with reference to Examples 1–4 set forth above, that it provides an effective process and installation for the fluorination or perfluorination of a hydrocarbon substrate, which promise to provide good product yields, particularly when optimized, in an easily carried out and practical fashion which is economically competitive.

What is claimed is:

1. A process for the fluoridation of a hydrocarbon substrate, the process comprising the steps of:

diluting a hydrocarbon substrate feed with an inert diluent liquid to form a diluted substrate;

mixing the diluted substrate with a gaseous fluorinating reagent to form a reaction mixture which is a foam;

allowing the fluorinating reagent to react in the foam with the substrate, to fluorinate the substrate to obtain fluorinated product material;

separating the foam containing the fluorinated product material into a gas component and a liquid component, the liquid component containing the fluorinated product material;

withdrawing the fluorinated product material form the liquid component and returning the liquid component from which the fluorinated product material has been withdrawn to the diluting step where it acts as the diluent liquid;

feeding a feed of the fluorinating reagent into the gas component; and recirculating the gas component containing the fluorinating reagent feed to the mixing step where it provides the fluorinating reagent in the reaction mixture.

2. A process as claimed in claim 1, in which the feeding to the hydrocarbon substrate feed is into a stream of the liquid component which is undergoing turbulent flow, the feeding of the hydrocarbon substrate being at a position between the separating step and the mixing step.

3. A process as claimed in claim 2, in which returning the liquid component to the diluting step is by pumping the liquid component at a rate sufficient to cause turbulent flow in the pumped liquid component, the hydrocarbon substrate feed being fed into the turbulent flow of the pumped liquid component with the hydrocarbon substrate feed in liquid form.

4. A process as claimed in claim 1, in which the mixing is by means of a mixing step which progresses substantially to completion in at most 1 second.

5. A process as claimed in claim 1, in which the gaseous fluorinating reagent is selected from the group of fluorinating gases consisting of $F_2$, $UF_6$, $XeF_2$, $ClF_3$ and $BrF_3$.

6. A process as claimed in claim 1, in which the gaseous fluorinating reagent, when it is mixed with the diluted substrate, is also in diluted form, the gaseous fluorinating reagent being diluted with an inert diluent gas.

7. A process as claimed in claim 5, in which the gaseous fluorinating reagent is $F_2$, being in the form of part of an essentially $F_2/N_2$ gas mixture in which $N_2$ is an inert diluent gas, when the gaseous fluorinating reagent is mixed with the diluted substrate, the gas mixture including 10–80% by volume $F_2$ and 20–90% by volume $N_2$, the volume ratio in the mixing step of the gas mixture:diluted substrate being 2:1–1:50 by volume.

8. A process as claimed in claim 1, in which allowing the fluorinating reagent to react in the foam with the substrate includes causing the reaction mixture to pass, in the form of a foam, along a flow path leading from the mixing step to the separating step, the flow path being inclined at an angle to the horizontal and the fluorinating agent reacting in the foam with the substrate as the foam moves along the flow path.

9. A process as claimed in claim 8, in which the flow path is inclined by an angle of at least 45° to the horizontal, the numerical ratio of the cross-sectional flow area in mm² of the flow path to its length in mm being in the range $\pi/4{:}15$–$\pi/4{:}40$.

10. A process as claimed in claim 1, in which the separating step is a settling step in which the foam is allowed to settle into a layer of liquid component below a header space containing the gas component, fluorinated product material and returned liquid component being withdrawn from the liquid layer, recirculated gas component being withdrawn from the header space, and a feed of the gaseous fluorinating reagent being fed into the header space.

11. A process as claimed in claim 10, in which the fluorinated product material and returned liquid component are withdrawn as a mixture from the liquid layer, the process including separating the fluorinated product material from the liquid component after withdrawal thereof from the liquid layer and before the liquid component enters the diluting step in which it dilutes the substrate feed.

12. A process as claimed in claim 1, in which the residence time of the liquid component in the separating step and the residence time of the liquid component in the liquid component returning step, after the liquid component leaves the separating step and until it enters the mixing step, amount in total to at most 10 seconds.

13. A process as claimed in claim 1, in which allowing the fluorinating reagent to react in the foam with the hydrocarbon substrate at a reaction pressure of 200–700 kPa and at a reaction temperature of between −30° C. and 50° C.

14. A process as claimed in claim 1, in which the feeding of the hydrocarbon substrate feed into the inert diluent liquid is in a proportion such that a dilution of the substrate by the diluent liquid is obtained whereby the volume ratio of substrate:diluent liquid in the diluted substrate is in the range of 1:50 000–1:300 000.

15. A process as claimed in claim 1, in which the substrate is selected from the group of unsubstitued hydrocarbons consisting of alkyl compounds and aryl compounds, and from the group of substituted hydrocarbons consisting of halogenated hydrocarbons, carboxylic acid halides, sulphonic acid halides, esters and ethers.

16. A process as claimed in claim 1, in which the inert diluent liquid is hydrogen fluoride (HF).

* * * * *

UNITED STATES PATENT AND TRADEMARK OFFICE
CERTIFICATE OF CORRECTION

PATENT NO. : 6,288,291 B1  
DATED : September 11, 2001  
INVENTOR(S) : Driekus Van Der Westhuizen et al.

It is certified that error appears in the above-identified patent and that said Letters Patent is hereby corrected as shown below:

<u>Title page,</u>
Item [73], after "Energy" insert -- Corporation Ltd., Pelindaba --.

Signed and Sealed this

Thirtieth Day of July, 2002

Attest:

Attesting Officer

JAMES E. ROGAN
Director of the United States Patent and Trademark Office